United States Patent [19]
Portney

[11] Patent Number: 6,126,286
[45] Date of Patent: *Oct. 3, 2000

[54] ENHANCED MONOFOCAL OPHTHALMIC LENS

[75] Inventor: Valdemar Portney, Tustin, Calif.

[73] Assignee: Allergan, Waco, Tex.

[*] Notice: This patent is subject to a terminal disclaimer.

[21] Appl. No.: 09/302,235

[22] Filed: Apr. 29, 1999

Related U.S. Application Data

[62] Division of application No. 09/014,310, Jan. 27, 1998, Pat. No. 6,024,447, which is a continuation of application No. 08/651,017, May 21, 1996, Pat. No. 5,864,378.

[51] Int. Cl.$^7$ ................................. G02C 7/04; A61F 2/16

[52] U.S. Cl. ................................. 351/160 R; 351/160 H; 623/6.28

[58] Field of Search ........................... 351/160 R, 160 H, 351/161, 162; 623/6, 6.11, 6.27, 6.28, 6.29

[56] References Cited

U.S. PATENT DOCUMENTS

| | | | |
|---|---|---|---|
| Re. 25,286 | 11/1962 | DeCarle | 351/161 |
| 1,483,509 | 2/1924 | Bugbee | 65/39 |
| 2,129,305 | 9/1938 | Feinbloom | 351/162 |

(List continued on next page.)

FOREIGN PATENT DOCUMENTS

| | | |
|---|---|---|
| 3225789 | 10/1989 | Australia . |
| 159395 | 4/1914 | Canada . |
| 0140063 | 9/1984 | European Pat. Off. . |

(List continued on next page.)

OTHER PUBLICATIONS

"A Three–Part System For Refining Intraocular Lens Power Calculations", *Journal of Cataract and Refractive Surgery*, J.T. Holladay, M.D., et al, vol. 14, Jan. 1988, pp. 17–23.

"The Shah Bifocal Intraocular Lens Implant", Shah & Shah Intraocular Lens Laboratories, Calcutta, India, pp. 1–11, No Date Available.

"Further Developments of Bifocal Contact Lenses", *Contacto*, John DeCarle, Jun., 1960, pp. 185–186.

"Contact Lens Practice", Robert B. Mandell, M.D., 4$^{th}$ Ed, 1988, pp. 211–212, 403–404, 491–492, & 792.

"Encyclopedia of Contact Lens Practice", Sep., 1960 pp. 24–26.

"Lens Design Fundamentals"; R. Kingslake; Institute of Optics University of Rochester, Rochester, NY; Academic Press 1978; pp. 36–39.

*Primary Examiner*—Georgia Epps
*Assistant Examiner*—Jordan M. Schwartz
*Attorney, Agent, or Firm*—Stout, Uxa, Buyan & Mullins, LLP; Frank J. Uxa

[57] ABSTRACT

An ophthalmic lens for providing a monofocal vision correction power with an enhanced depth of focus is adapted to be implanted into an eye, placed over the eye, or to be disposed in a cornea of the eye. The ophthalmic lens includes a baseline diopter power for far vision correction, a first zone having a first vision correction power, and a second zone having a second vision correction power. The second zone is located radially outwardly of the first zone. The first zone includes a near vision correction power, and the second zone includes a far vision correction power. A maximum diopter value of the first zone is approximately 0.7 diopters above the baseline diopter, and a minimum diopter value of the second zone is approximately 0.5 diopters below the baseline diopter power. The first zone is adapted for focusing light at a first predetermined distance from the retina of the user, and the second zone is adapted for focusing light at a second predetermined distance from the retina of the user. A third zone, which is substantially similar to the first zone, is located radially outwardly of the second zone, and a fourth zone, which is substantially similar to the second zone, is located radially outwardly of the third zone. A third vision correction power of the third zone is approximately the same as the first vision correction power of the first zone, and a fourth vision correction power of the fourth zone is approximately the same as the second vision correction power of the second zone.

9 Claims, 3 Drawing Sheets

U.S. PATENT DOCUMENTS

| | | | |
|---|---|---|---|
| 2,274,142 | 2/1942 | Houchin | 351/171 |
| 2,405,989 | 8/1946 | Beach | 351/169 |
| 2,511,517 | 6/1950 | Spiegel | 65/136.4 |
| 3,004,470 | 10/1961 | Ruhle | 359/721 |
| 3,031,927 | 5/1962 | Wesley | 351/161 |
| 3,034,403 | 5/1962 | Neefe | 351/162 |
| 3,210,894 | 10/1965 | Bentley | 451/42 |
| 3,227,507 | 1/1966 | Feinbloom | 351/160 R |
| 3,339,997 | 9/1967 | Wesley | 351/161 |
| 3,420,006 | 1/1969 | Barnett | 451/283 |
| 3,431,327 | 3/1969 | Tsuetaki | 264/1.8 |
| 3,482,906 | 12/1969 | Volk | 351/160 R |
| 3,542,461 | 11/1970 | Girard et al. | 351/160 R |
| 3,693,301 | 9/1972 | Lemaltre | 451/55 |
| 3,794,414 | 2/1974 | Wesley | 351/161 |
| 3,932,148 | 1/1976 | Krewalk, Sr. | 451/42 |
| 4,055,378 | 10/1977 | Feneberg et al. | 351/160 R |
| 4,062,629 | 12/1977 | Winthrop | 351/169 |
| 4,073,579 | 2/1978 | Deeg et al. | 351/169 |
| 4,195,919 | 4/1980 | Shelton | 351/160 R |
| 4,199,231 | 4/1980 | Evans | 351/160 H |
| 4,210,391 | 7/1980 | Cohen | 351/161 |
| 4,240,719 | 12/1980 | Guilino et al. | 351/169 |
| 4,274,717 | 6/1981 | Davenport | 351/169 |
| 4,307,945 | 12/1981 | Kitchen et al. | 351/169 |
| 4,315,673 | 2/1982 | Guilino et al. | 351/169 |
| 4,338,005 | 7/1982 | Cohen | 351/161 |
| 4,340,283 | 7/1982 | Cohen | 351/161 |
| 4,377,329 | 3/1983 | Polar | 351/160 R |
| 4,402,579 | 9/1983 | Polar | 351/160 R |
| 4,418,991 | 12/1983 | Breger | 351/161 |
| 4,504,982 | 3/1985 | Burk | 623/6 |
| 4,573,775 | 3/1986 | Bayshore | 351/161 |
| 4,580,882 | 4/1986 | Nuchman et al. | 351/161 |
| 4,596,578 | 6/1986 | Kelman | 623/6 |
| 4,618,228 | 10/1986 | Baron et al. | 351/161 |
| 4,618,229 | 10/1986 | Jacobstein et al. | 351/161 |
| 4,636,049 | 1/1987 | Blaker | 351/161 |
| 4,636,211 | 1/1987 | Nielsen et al. | 623/6 |
| 4,637,697 | 1/1987 | Freeman | 351/161 |
| 4,641,934 | 2/1987 | Freeman | 351/159 |
| 4,693,572 | 9/1987 | Tsuetaki et al. | 351/161 |
| 4,704,016 | 11/1987 | de Carle | 351/161 |
| 4,720,286 | 1/1988 | Bailey et al. | 623/6 |
| 4,752,123 | 6/1988 | Blaker | 351/161 |
| 4,759,762 | 7/1988 | Grendahl | 623/6 |
| 4,769,033 | 9/1988 | Nordan | 623/6 |
| 4,813,955 | 3/1989 | Achatz et al. | 623/6 |
| 4,830,481 | 5/1989 | Futhey et al. | 351/161 |
| 4,881,804 | 11/1989 | Cohen | 351/161 |
| 4,890,912 | 1/1990 | Visser | 351/161 |
| 4,890,913 | 1/1990 | DeCarle | 351/161 |
| 4,898,461 | 2/1990 | Portney | 351/169 |
| 4,917,681 | 4/1990 | Nordan | 623/6 |
| 4,919,663 | 4/1990 | Grendahl | 623/6 |
| 4,921,496 | 5/1990 | Grendahl | 623/6 |
| 4,923,296 | 5/1990 | Erickson | 351/161 |
| 4,938,583 | 7/1990 | Miller | 351/161 |
| 5,000,559 | 3/1991 | Takahashi et al. | 351/169 |
| 5,002,382 | 3/1991 | Seidner | 351/161 |
| 5,019,099 | 5/1991 | Nordan | 623/6 |
| 5,106,180 | 4/1992 | Marie et al. | 351/161 |
| 5,112,351 | 5/1992 | Christie et al. | 623/6 |
| 5,225,858 | 7/1993 | Portney | 351/161 |
| 5,260,727 | 11/1993 | Oksman et al. | 351/161 |
| 5,652,638 | 7/1997 | Roffman et al. | 351/161 |
| 5,684,560 | 11/1997 | Roffman et al. | 351/160 R |
| 5,864,378 | 1/1999 | Portney | 351/160 R |

FOREIGN PATENT DOCUMENTS

| | | |
|---|---|---|
| 0342895 | 11/1989 | European Pat. Off. . |
| 0351471 | 1/1990 | European Pat. Off. . |
| 0601845 | 6/1994 | European Pat. Off. . |
| 2702117 | 7/1978 | Germany . |
| 888414 | 11/1988 | South Africa . |
| 939016 | 4/1962 | United Kingdom . |
| 2058391A | 8/1980 | United Kingdom . |
| 2129155A | 5/1984 | United Kingdom . |
| 2146791A | 5/1984 | United Kingdom . |
| 2192291 | 1/1988 | United Kingdom . |
| WO86/03961 | 7/1986 | WIPO . |
| WO87/00299 | 1/1987 | WIPO . |
| WO87/07496 | 12/1987 | WIPO . |
| 8809950 | 12/1988 | WIPO . |
| 8902251 | 3/1989 | WIPO . |
| 8911672 | 11/1989 | WIPO . |
| 9000889 | 2/1990 | WIPO . |

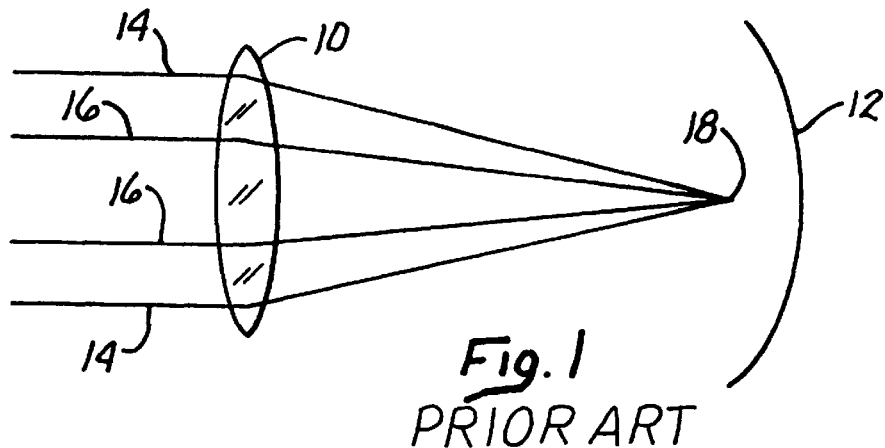
Fig. 1
PRIOR ART
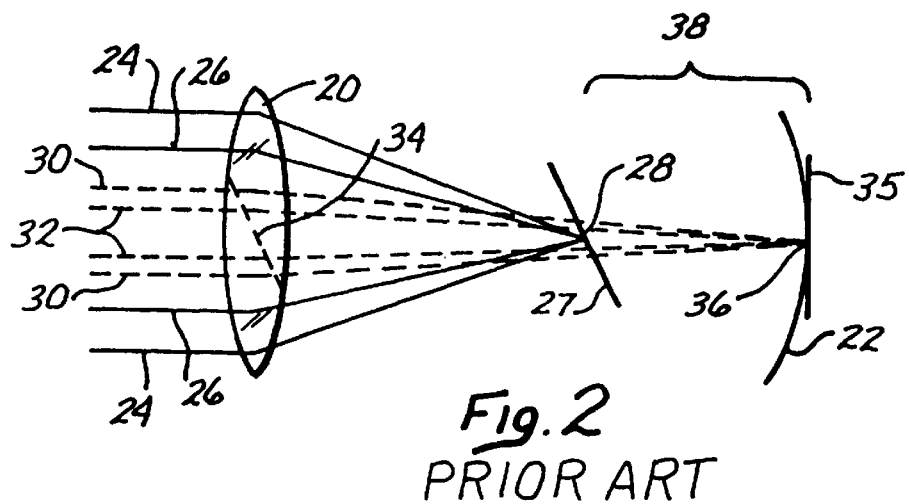
Fig. 2
PRIOR ART
Fig. 5
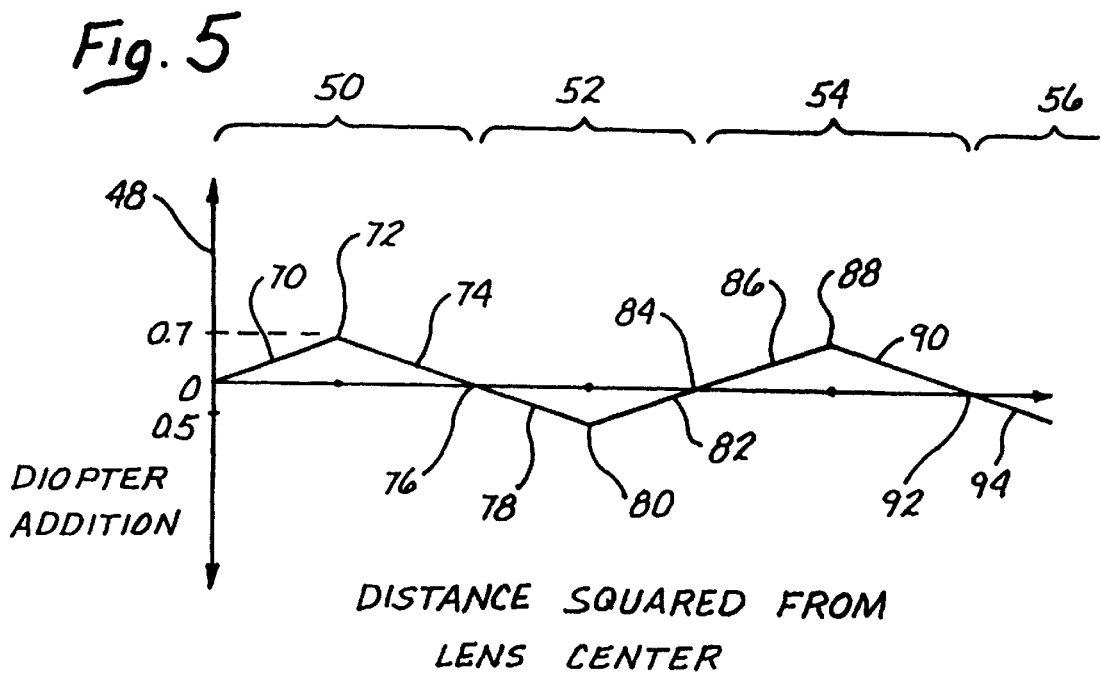
DISTANCE SQUARED FROM LENS CENTER

ENHANCED MONOFOCAL OPHTHALMIC LENS

This application is a division of application Ser. No. 09/014,310 filed, Jan. 27, 1998 now U.S. Pat. No. 6,024,447 which, in turn, is a continuation of application Ser. No. 08/651,017, filed May 21, 1996, now U.S. Pat. No. 5,864,378 the entire disclosure of each of which is hereby incorporated by reference herein.

BACKGROUND OF THE INVENTION

1. Field of the Invention

The present invention relates generally to ophthalmic lenses and, more particularly, to a monofocal ophthalmic lens having an enhanced depth of focus.

2. Description of Related Art

Monofocal ophthalmic lenses provide a single vision correction diopter power. When a prescription does not require any astigmatism correction, and when the prescription can be accurately applied without error, monofocal ophthalmic lenses can provide excellent image quality to the patient. In reality, an exact power prescription for any given patient is often difficult to achieve. Surgeons are facing increasing demand to improve intraocular lens (IOL) power predictions in cataract surgery, for example. Spherical errors within plus or minus 0.5 diopters occur in approximately fifty percent of these cases, and spherical errors within a range of plus or minus 1 diopter occur in approximately ninety percent of these cases.

An inherent variability associated with intraocular lens power calculations results from uncertainties of the parameters of any given ocular system, such as axial length, intraocular lens location, corneal diopter, and intraocular lens tilt and/or decentration. As a result of this inherent variability, the excellent image quality achievable by monofocal intraocular lenses is often obtained at the expense of subsequent, additional refractive correction after the initial implantation of the monofocal intraocular lens.

FIG. 1 illustrates a conventional monofocal ophthalmic lens 10, which has been implanted with a spherical error of approximately 0.5 diopters. This spherical error prevents the parallel incoming light from being focused by the monofocal ophthalmic lens 10 near a retina 12 of the eye of a user. The parallel incoming light comprises peripheral rays 14 and intermediate rays 16, all of which are refracted by the monofocal ophthalmic lens 10 onto the focus point 18. In the illustration of FIG. 1, the spherical refractive error is equal to approximately 0.5 diopters. If the spherical refractive error were greater, light would be focused at a point closer to the monofocal ophthalmic lens 10, between the monofocal ophthalmic lens 10 and the retina 12. If the spherical refractive error were positive, light would be focused behind the retina 12, at a distance proportional to the magnitude of the positive spherical refractive error.

Although the parallel incoming light is refracted only about 0.5 diopters in front of the retina 12, the quality of image perceived by the user is drastically reduced. This quality of image is further reduced as the magnitude of the refractive error increases. Thus, although the monofocal ophthalmic lens 10 is capable of providing excellent image quality correction, the image quality can only be obtained within a relatively narrow depth of focus. The monofocal ophthalmic lens 10 must thus focus the parallel incoming light very close to the retina 12 in order to obtain high image quality. Consequently, the optical quality of the monofocal ophthalmic lens 10 is very sensitive to spherical refractive error.

Turning to FIG. 2, the conventional monofocal ophthalmic lens 20 is shown focusing parallel incoming light onto and near a retina 12. The eye of this illustration comprises a slight cylinder or astigmatism. Although the cylinder generally may comprise curvatures about a number of differently oriented axes, the cylinder of the eye in FIG. 2 comprises a vertical curvature that is different from a horizontal curvature. The solid lines 24 and 26 in FIG. 2 illustrate the refraction of parallel incoming light through a vertical cross section of the monofocal ophthalmic lens 20, and the dashed lines 30 and 32 illustrate the refraction of parallel incoming light through a horizontal cross section of the multifocal ophthalmic lens 20.

The parallel incoming light passing through the vertical cross section of the multifocal ophthalmic lens 20 comprises peripheral rays 24 and intermediate rays 26, all of which are focused along a sagittal line of focus 27. The sagittal line of focus is perpendicular to a plane on which FIG. 2 is drawn. For the purposes of illustration, the peripheral rays 24 and the intermediate rays 26 are shown focused at a point 28 on the sagittal line of focus 27, which is located between the monofocal ophthalmic lens 20 and the retina 22. Since the peripheral rays 24 and the intermediate rays 26 are not focused onto the retina 22, the cylinder of the eye comprises a negative diopter. If the peripheral rays 24 and the intermediate rays 26 were focused by the monofocal ophthalmic lens 20 behind the retina 22, then a positive cylinder diopter error would exist about the vertical axis.

In the illustration of FIG. 2, the peripheral rays 30 and the intermediate rays 32 passing through a horizontal cross section 34 of the monofocal ophthalmic lens 20 are focused onto the tangential line of focus 35. The peripheral rays 30 and the intermediate rays 32 are shown in the figure focused at a point 36 along the tangential line of focus 35. Since the tangential line of focus 35 passes through the retina 22, very little diopter error exists along the horizontal cross section 34 of the eye. The peripheral rays 30 and the intermediate rays 32 would focus in front of the retina 22 in the case of a positive diopter error along the horizontal cross section 34, and would focus behind the retina 22 in the case of a negative diopter error along the horizontal cross section 34.

The distance between the sagittal line of focus 27 and the tangential line of focus 35 is referred to as the cylinder power. This astigmatism may be corrected by adding cylinder power and spherical power. More particularly, cylinder power, which is opposite to the existing cylinders is added, to thereby collapse the sagittal line of focus 27 and the tangential line of focus 35 into a single point located between the sagittal line of focus 27 and the tangential line of focus 35. Spherical power is then added to bring this single point onto the retina 22. Similarly to the inherent variabilities discussed above with reference to FIG. 1, precise astigmatism correction is often difficult to achieve. In the case of an intraocular lens having a torric surface for astigmatism correction of the cornea, the use of the torric surface with the regular spherical intraocular lens suffers from a number of inherent problems.

An object of a conventional torric intraocular lens, for example, is to reduce the preexisting cylinder and, as a result, to reduce spectacle dependency. The torric intraocular lens, however, may increase the spherical error of the system and still require the subject to wear glasses. As an example, if a minus 3 diopter cylinder is used to correct a plus 3 corneal cylinder and the torric intraocular lens is rotationally misaligned by 30 degrees, then the ocular system will suffer an approximately negative 0.5 diopter spherical shift from the targeted condition of the perfect alignment. This spherical shift is clinically significant, and even lesser spherical errors may be uncomfortable to the patient. A need has thus existed in the prior art of both monofocal and torric ophthalmic lenses for a device capable of reducing the sensitivity to refractive errors of these lenses.

SUMMARY OF THE INVENTION

The ophthalmic lens for monofocal prescription of the present invention provides an enhanced depth of focus, to thereby reduce the traditional sensitivity to spherical refractive errors associated with monofocal ophthalmic lenses. This enhanced depth of focus is provided by the introduction of power deviations from the baseline diopter power along the radial direction of the monofocal ophthalmic lens. These power deviations serve to distribute the focal points of parallel incoming rays about a predetermined distance from the original focal point. In effect, the deviations in diopter power along the direction of the monofocal ophthalmic lens introduce a depth of focus to the monofocal ophthalmic lens.

According to one aspect of the present invention, an ophthalmic lens for providing a monofocal vision correction power with an enhanced depth of focus is adapted to be implanted into an eye, placed over the eye, or to be disposed in a cornea of the eye. The ophthalmic lens includes a baseline diopter power for far vision correction, a first zone having a first vision correction power, and a second zone having a second vision correction power. The second zone is located radially outwardly of the first zone. The first zone includes a near vision correction power, and the second zone includes a far vision correction power. A maximum diopter value of the first zone is approximately 0.7 diopters above the baseline diopter, and a minimum diopter value of the second zone is approximately 0.5 diopters below the baseline diopter power. The first zone is adapted for focusing light at a first predetermined distance from the retina of the user, and the second zone is adapted for focusing light at a second predetermined distance from the retina of the user. The second predetermined distance is approximately opposite and equal to the first predetermined distance. A third zone, which is substantially similar to the first zone, is located radially outwardly of the second zone, and a fourth zone, which is substantially similar to the second zone, is located radially outwardly of the third zone. A third vision correction power of the third zone is approximately the same as the first vision correction power of the first zone, and a fourth vision correction power of the fourth zone is approximately the same as the second vision correction power of the second zone. In addition to the third and fourth zones, similarly configured fifth and sixth zones are located radially outwardly of the third and fourth zones. Similarly configured seventh and eighth zones may be located radially outwardly of the fifth and sixth zones. Additional pairs of zones may be located radially outwardly of the seventh and eighth zones.

According to another aspect of the present invention, an ophthalmic lens for providing a monofocal vision correction power with enhanced depth of focus includes a baseline diopter power for far vision correction. The ophthalmic lens includes a single set of alternating positive and negative vision correction powers, which repeats along a radially outwardly direction from an optical axis of the ophthalmic lens. The single set of alternative positive and negative vision correction powers may correspond, for example, to the first and second zones mentioned above.

According to yet another aspect of the present invention, an ophthalmic lens for providing a monofocal vision correction power with an enhanced depth of focus includes an inner zone, an intermediate zone, and an outer zone. The inner zone has a vision correction power that progressively changes along a radially outwardly direction to a first diopter value, and the intermediate zone has a vision correction power that progressively changes along a radially outwardly direction to a second diopter value. The intermediate zone circumscribes the inner zone. A square of a distance between the first diopter value and an optical axis of the ophthalmic lens is approximately half of a square of a distance between the second diopter value and the optical axis of the ophthalmic lens. The outer zone circumscribes the intermediate zone and has a vision correction power that progressively changes along a radially outwardly direction back to the first diopter value. A square of a width of the outer zone is approximately equal to a square of the width of the intermediate zone. The ophthalmic lens further includes a second intermediate zone, which circumscribes the outer zone, and which has a vision correction power that ramps along a radially outwardly direction back to the second diopter value. A square of a width of the second intermediate zone is approximately equal to a square of the width of the outer zone. The first diopter value may be positive, and the second diopter value may be negative. A magnitude of the first diopter value is approximately 1.4 times a magnitude of the second diopter value.

The present invention, together with additional features and advantages thereof, may best be understood by reference to the following description taken in connection with the accompanying illustrative drawings.

BRIEF DESCRIPTION OF THE FIGURES

FIG. 1 is a schematic view illustrating the focusing of light of the prior art monofocal ophthalmic lens near a retina;

FIG. 2 is a schematic view illustrating the focusing of light of a prior art monofocal ophthalmic lens located within an eye having an astigmatism;

FIG. 5 is a plot of the power of the optic versus the square of the distance from the optic axis for the intraocular monofocal ophthalmic lens having an enhanced depth of focus, according to the presently preferred embodiment;

DETAILED DESCRIPTION OF THE PREFERRED EMBODIMENTS

Figure 3:
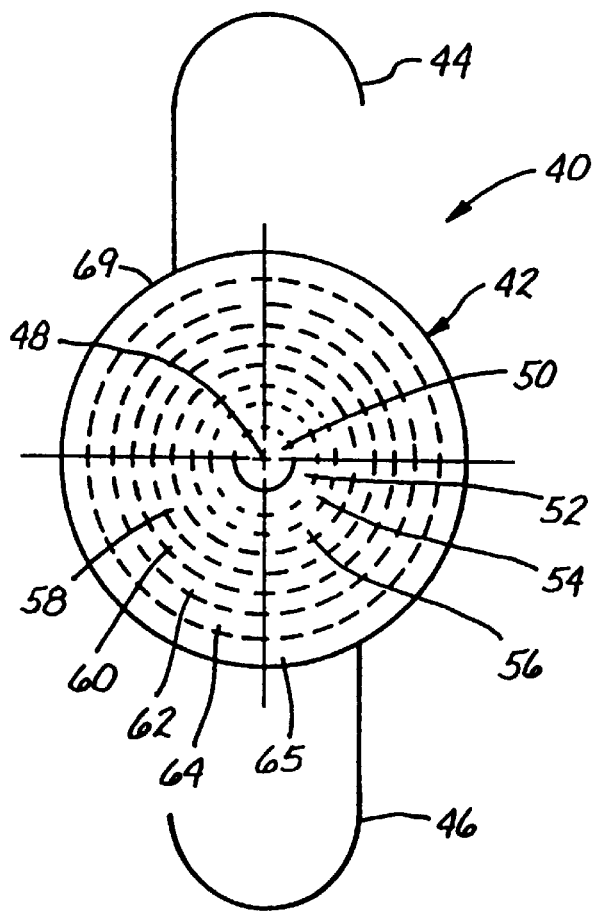
FIG. 3 is a plan view of an intraocular monofocal ophthalmic lens having an enhanced depth of focus, according to the presently preferred embodiment.
Figure 4:
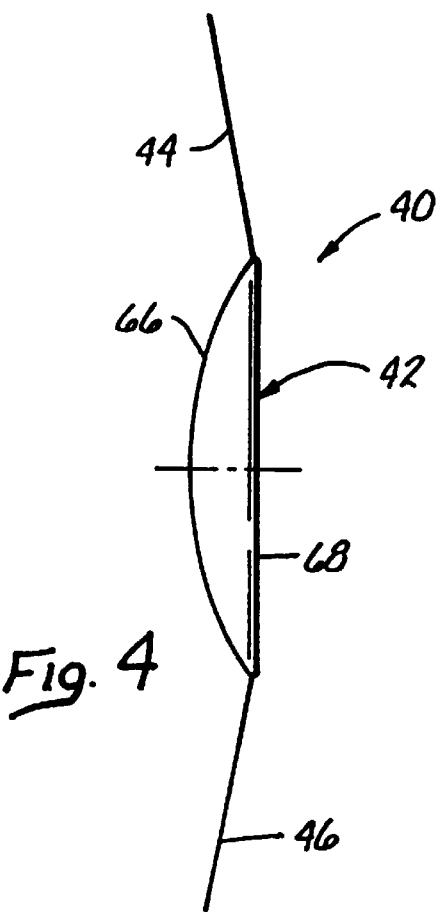
FIG. 4 is a side elevational view of the intraocular monofocal ophthalmic lens having an enhanced depth of focus, according to the presently preferred embodiment.

FIGS. 3 and 4 illustrate an enhanced depth of focus monofocal ophthalmic lens 40, which comprises a circular optic 42 and two fixation members 44 and 46. The circular optic 42 may be constructed of rigid biocompatible materials, such as polymethylmethacrylate (PMMA), or flexible, deformable materials, such as silicone, hydrogel and the like which enable the circular optic 42 to be rolled or folded for insertion through a small incision into the eye.

In the presently preferred embodiment, the fixation members 44 and 46 are fine hair-like strands or filaments which are attached to the circular optic 42 using conventional techniques. The fixation members 44 and 46 may be constructed of a suitable polymeric material, such as PMMA or polypropylene. Alternatively, the fixation members 44 and 46 may be integral with the circular optic 42. The circular optic 42 and the fixation members 44 and 46 may of any desired number and configuration, and the configurations illustrated are purely illustrative.

The circular optic 42 has an optical axis 48, and a number of optical zones. In the presently preferred embodiment, the peripheries of the optical zones are circular. The optical zones comprise a first zone 50, a second annular zone 52, a third annular zone 54, a fourth annular zone 56, a fifth annular zone 58, a sixth annular zone 60, a seventh annular zone 62, an eight annular zone 64, and a ninth annular zone 65. The optical zones 50–65 circumscribe the optical axis 48, and the optical zones are contiguous. The optical zones 50–65 are concentric and coaxial with the circular optic 42.

The optical zones 50–65 are used in describing the vision correction of the circular optic 42, and they are arbitrarily defined. Thus, the peripheries of the optical zones 50–65 and the number of optical zones may be selected as desired. For example, only a first zone 50 and a second annular zone 52 may be used. To facilitate describing the circular optic 42, the peripheries of the optical zones 50–65 are considered to be the zero crossings in FIG. 5. Although the boundaries of the optical zones 50–65 are indicated by phantom lines in FIG. 3, it should be understood that the circular optic 42 has no such lines in any of its surfaces and that these lines constitute reference lines which define the optical zones 50–65.

As shown in FIG. 4, the circular optic 42 comprises a convex anterior surface 66 and a planar posterior surface 68; however, these configurations are merely illustrative. Although the vision correction power may be placed on either of the surfaces 66 and 68, in the presently preferred embodiment, the anterior surface 66 is appropriately shaped to provide the desired vision correction powers.

FIG. 5 illustrates the preferred manner in which the vision correction power of the circular optic 42 varies from the optical axis 48 of the circular optic 42 to the circular outer periphery 69 (FIG. 3) of the optic. A preferred power distribution curve for a corneal inlay may be similar, or identical, to the curve of FIG. 5.

In FIG. 5, the vertical or "y" axis represents the variation in diopter power of the circular optic 42 from the baseline or far vision correction power, and the "x" or horizontal axis shows the distance outwardly from the optical axis 48 in millimeters. The units of this horizontal axis are expressed in square of the actual distance. Thus, a distance of four units on the horizontal axis corresponds to an actual distance on the lens of two units. In the presently preferred embodiment, the areas of each of the optical zones 50–65 are approximately equal to each other. The zero-diopter or baseline power of FIG. 5 is the power required for far vision for a conventional monofocal intraocular lens. The power variation shown in FIG. 5 is applicable to any radial plane passing through the optical axis 48. In other words, the power at any given radial distance from the optical axis 48 is the same.

The first zone 50 extends from the optical axis 48 to a circular periphery 76, the second annular zone 52 extends from the circular periphery 76 to a circular periphery 84, and the third annular zone 54 is considered as extending from the circular periphery 84 to the circular periphery 92. The fourth, fifth, sixth, seventh, eighth, and ninth annular zones 56–65 are not shown in FIG. 5, but are similarly configured to the zones shown in that figure. The negative diopter powers of the second, fourth, sixth, and eight zones are of less power than required for far vision, and may be considered as far, far vision powers. As shown in FIG. 5, the vision correction power crosses the "x" axis or baseline diopter power at the circular peripheries 76, 84, and 92.

The vision correction power of the first zone 50 varies progressively and continuously from the baseline diopter power at the optical axis 48 to a first diopter value 72, which is approximately 0.7 diopters in the presently preferred embodiment. The vision correction power in this first zone 50 then decreases continuously and progressively from the first diopter value 72 back to the baseline diopter power at the first circular periphery 76. Thus, the vision correction power of the first zone 50 comprises an increasing progressively change 70, which transitions at the first diopter value 72 into a decreasing progressively change 74. The second annular zone 52 begins at the first circular periphery 76, and comprises a decreasing progressively change 78, which terminates at a second diopter value 80. In the presently preferred embodiment, a second diopter value 80 comprises a negative 0.5 diopter power. Of course, the diopters shown on the ordinate in FIG. 5 are merely exemplary, and actual correction provided can vary with desired parameters and the prescription needs of the patient. The magnitude of the first diopter value 72 of 0.7 diopters is approximately 1.4 times the magnitude of the second diopter value 80 of –0.5 diopters. The selection of the first diopter value 72 and the second diopter value 80 corresponds to the focusing of light either in front of or behind the focal point of light of the baseline diopter value. For example, the first diopter value 72 may be increased to focus light a greater distance in front of the focal point of the baseline diopter value and, similarly, the magnitude of the second diopter value 80 may be decreased to focus light a greater distance behind the focal point of the baseline diopter value. In the presently preferred embodiment, the magnitude of the first diopter value 72 and the magnitude of the second diopter value 80 are selected to focus light at equal and opposite distances from the focal point of the baseline diopter value.

In the presently preferred embodiment, the vision correction power of the third annular zone 54 is substantially similar to the vision correction power of the first zone 50. Thus, the increasing progressively change 86, the third diopter value 88 and the decreasing progressively change 90 of the third annular zone 54 are approximately equal to the increasing progressively change 70, the first diopter value 72, and the decreasing progressively change 74 of the first zone 50. Similarly, in the presently preferred embodiment, the fourth annular zone 56 is substantially similar to the second annular zone 52. Moreover, the fifth, seventh, and ninth annular zones 58, 62, and 65 are configured similarly to the first zone 50; and the fourth, sixth, and eight annular zones 56, 60, and 64 are configured similarly to the second annular zone 52.

Although the diopter additions shown in FIG. 5 resemble a sawtooth configuration on the distance-squared horizontal axis, other configurations, such as a sinusoidal variation, may be implemented according to desired parameters. Moreover, the configurations of the third through ninth annular zones 54–65 do need to be substantially the same as the configurations of the first and second zones 50 and 52, respectively. Of course, the number of annular zones may be changed, as well. For example, a number of annular zones less than nine, or greater than nine, may be implemented.

The sawtooth configuration of the presently preferred embodiment introduces asymmetry, which is presently preferred. Advantages to utilizing surface asphericity are to expand depth of focus and to insure continuity of image quality within a certain diopter range. Thus, the introduction of the positive diopter values by the first, third, fifth, seventh, and ninth zones 50, 54, 58, 62, and 65, and of the negative diopter additions by the second, fourth, sixth, and eighth annular zones 52, 56, 60, and 64, increases the depth of focus of a conventional monofocal ophthalmic lens. Although these diopter additions and subtractions may slightly decrease the vision quality perceived by the patient, the depth of focus enhancement operates to ensure continuity of image within a certain diopter range. Thus, different sizes, fits, and/or changes in refractive prescription are accommodated.

A simple bifocal construction, where only a first zone 50 and a second annular zone 52 are used, may create some discontinuity between the peaks, which may be undesirable due to the artificial nature of the resulting human vision. Additionally, only a few positive and negative diopter addition zones (such as the first zone 50 and second annular zone 52) may unnecessarily introduce a factor of pupil dependency on the optical performance. For example, small pupil sizes corresponding to bright lighting conditions may render a significant portion of a second annular zone inoperative in a simple bifocal construction, since light does not travel therethrough. The use of many positive and negative diopter addition zones 50–65 of the present invention reduces the pupil dependency of the optical performance. Accordingly, the positive and negative diopter addition zones 50–65 of the present invention combine repeatability of the multifocal distribution over the surface of the circular optic 42 with asphericity (array type surface).

The positive diopter addition zones 50, 54, 58, 62, and 65 and the diopter substraction zones 52, 56, 60, and 64 serve to increase the depth of focus of the circular optic 42. This increased depth of focus reduces the sensitivity to the best focus position that is commonly associated with monofocal intraocular lenses. Although, theoretically, a slight reduction in the best quality image may occur, this slight reduction is often imperceivable by the patient. Since the vision of the patient is limited by the quality of the patient's retina, the actual reduction in best quality image is likely to not even be perceived by the patient. As an example, multifocal intraocular lenses which comprise diopter addition zones that introduce up to 3.5 diopters to the base diopter power have clinically demonstrated quite comparative image quality. These multifocal intraocular lenses introduce depths of focus of approximately 5 diopters by the addition of the 3.5 diopters above the baseline diopter power. Clinically significant reductions in image quality, defined by contrast sensitivity, were reported only for very low contrast charts. This data indicates that retina imaging function is a limited factor in optical perception, particularly for elderly persons where the retina is not able to detect small reductions in best quality image. Accordingly, a range of acceptable variation of the optical quality of dioptric component of the ocular system, or best quality image, is presented with each patient. The optical quality of the ophthalmic lens 40 of the present invention lies between a perfectly fitted monofocal intraocular lens and a multifocal intraocular lens, since the added diopter power of the present invention is less than half of the diopter power for a multifocal intraocular lens.

The optical quality of the intraocular lens 40 of the present invention should be closer to the optical quality of a monofocal intraocular lens than to the optical quality of a multifocal intraocular lens, in terms of modular transfer function (MTF). The modular transfer function is used to measure contrast, and typically comprises a plot of contrast versus size of the object, where small objects are not as sharp and larger objects have a greater contrast. The enhanced depth of focus monofocal ophthalmic lens 40 the present invention can provide a 1.5 to 2 diopter depth of focus addition, by the introduction of a 1 to 1.5 diopter range of variance added to the baseline diopter power.

Figure 6:
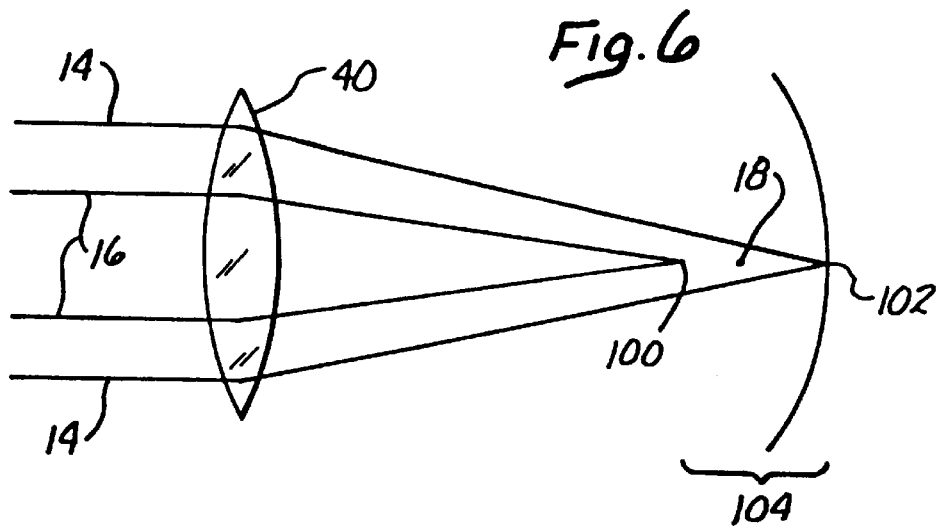
FIG. 6 is a schematic view illustrating the enhanced depth of focus monofocal ophthalmic lens of the presently preferred embodiment.

FIG. 6 illustrates the optic 40 of an enhanced depth of focus monofocal ophthalmic lens 42, having a baseline diopter power that is the same as the baseline diopter power of the monofocal ophthalmic lens 10 of FIG. 1. Light passing through the enhanced depth of focus monofocal ophthalmic lens 42 is focused within a range around the focus point 18. Parallel incoming rays 16 passing through the first, third, fifth, seventh, and ninth annular zones 50, 54, 58, 62, and 65 are focused between the focus point 18 and the focus point 100. Parallel incoming rays 14 passing through the second, fourth, sixth, and eighth zones 52, 56, 60, and 64 are focused between the focus point 18 and the focus point 102. Thus, the focus of the ophthalmic lens 42 is moved in both directions about the focus point 18 to provide an enhanced depth of focus to the monofocal ophthalmic lens 10 of FIG. 1.

Although the focus of light by the monofocal ophthalmic lens 10 onto the focus point 18 drastically reduces the quality of image perceived by the patient, the distribution of light between the focus points 100 and 102 of FIG. 6 very frequently results in an acceptable quality of image perceived by the patient. In fact, the quality of image provided by the ophthalmic lens 42 of FIG. 6 is often perceived by the patient to be just as good as the quality of image generated by a perfectly fitted monofocal ophthalmic lens 10 of FIG. 1.

Figure 7:
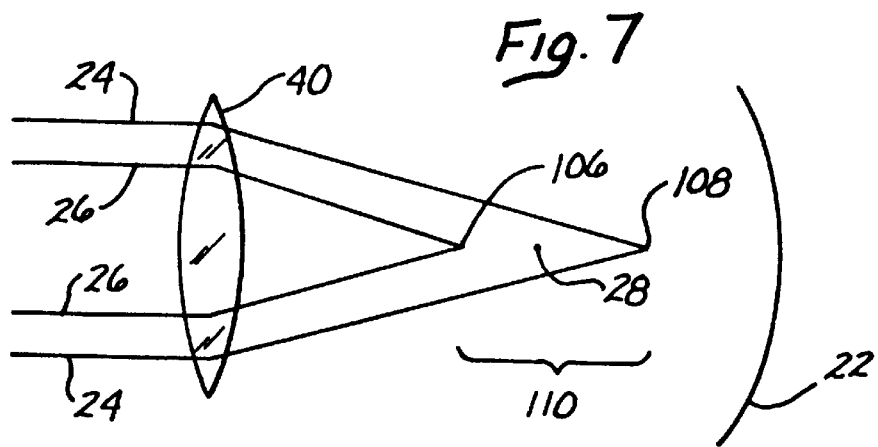
FIG. 7 is a schematic view illustrating a vertical cross-sectional view of light refracted through the enhanced depth of focus monofocal ophthalmic lens of the presently preferred embodiment within an eye having an astigmatism.
Figure 8:
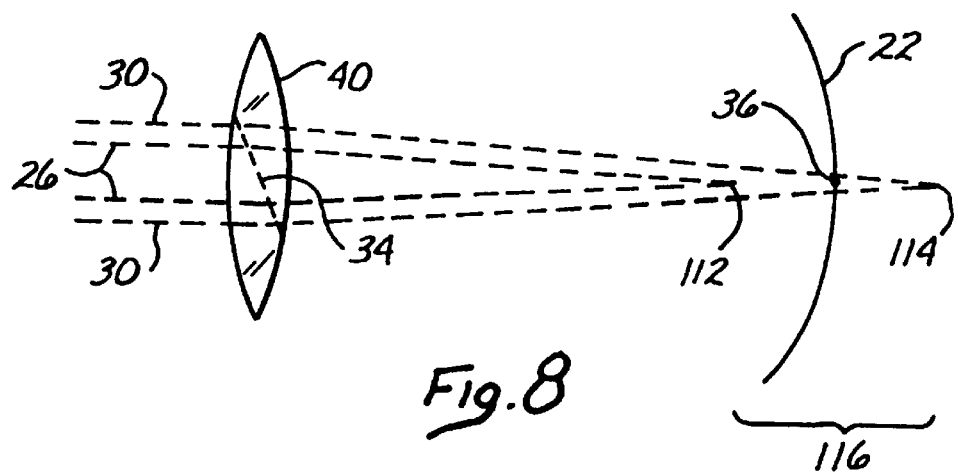
FIG. 8 is a schematic view illustrating a horizontal cross sectional view of light refracted through the enhanced depth of focus monofocal ophthalmic lens of the presently preferred embodiment, within an eye having an astigmatism.

Turning to FIGS. 7 and 8, the optic of an enhanced depth of focus monofocal ophthalmic lens 42 is shown refracting light across a vertical cross section and a horizontal cross section of the ophthalmic lens 42. The parallel incoming rays 24 pass through the diopter addition zones 50, 54, 58, 62, and 65, and the parallel incoming rays 26 pass through the diopter subtraction zones 52, 56, 60, and 64. The parallel incoming rays 24 and 26 are spread about the sagittal line of focus 27, but the sagittal line of focus 27 is attenuated. For purposes of illustration, only a point 28 along the sagittal line of focus 27 is shown. The parallel incoming rays 26 passing through the diopter substraction zones are focused between the point 28 and a focus point 108, and the parallel incoming rays 24 passing through the diopter addition zones are focused between the point 28 and the focus point 106. A distribution of rays around the point 28 is thus obtained, to achieve a depth of focus. Similarly, in the horizontal cross section of incoming parallel rays shown in FIG. 8, the rays 30 passing through the diopter subtraction zones are focused between the point 36 and the focus point 114, and the parallel incoming rays 26 passing through the diopter addition zones are focused between the point 36 and the focus point 112. The sagittal and tangential lines of focus of FIG. 2 are attenuated, but are not shown in FIGS. 7 and 8.

In contrast to the focusing of hardly any light between the point 28 and the point 36 by the monofocal ophthalmic lens 20 in FIG. 2, the ophthalmic lens 40 of the present invention focuses a relatively large amount of light between these two points 28 and 36. In particular, the light focusing distribution 110 of FIG. 7 extends half way into the amount of astigmatism 38, and the light distribution range 116 of FIG. 8 also extends half way into the amount of astigmatism 38. The baseline diopter power of the ophthalmic lens 40 of the present invention shown in FIGS. 7 and 8 may be slightly increased, if preferred. By covering the range of astigmatism 38, the ophthalmic lens 40 of the present invention reduces the sensitivity to astigmatism. The overlap of the light distribution 110 of FIG. 7 and the light distribution 116 of FIG. 8 within the range of cylinder 38 creates a continuous image to thereby reduce the sensitivity to astigmatism. The reduction to astigmatism sensitivity provided by the ophthalmic lens 40 of the present invention is especially advantageous to small cylinders 38. Additionally, this ophthalmic lens 40 can be successfully used with irregular astigmatisms having angles between cylinder meridians other than 90 degrees, and/or portions of the cornea having irregular dioptric powers. Conventional lenses cannot easily correct these irregular astigmatisms, but the present invention can be very effective in reducing the impact of these small irregular astigmatisms.

The enhanced depth of focus monofocal ophthalmic lens 40 of the present invention may be used in a variety of different applications, such as in refractive procedures, such as photorefractive keratotomy (PRK), which is a surgical technique where a laser is used to remove anterior layers of the cornea to modify the curvature of the cornea and thereby change the refractive power of the cornea. The present invention may be implemented to compensate for post-op refractive regression by producing a corneal surface with slightly extended diopter range, corresponding to diopter addition zones and diopter subtraction zones. The present invention can similarly be used in connection with contact lenses.

The magnitude of the diopter addition zones and the diopter substraction zones may be determined empirically before implementation of the present invention. The patient can be tested on the acceptable range of image quality by the introduction of simple defocus or cylinder to the patient's prescription. The patient can then indicate which amounts of defocus or cylinder are acceptable, before a discernable reduction in image quality is perceived by the patient. Thus, an acceptable range of extended depth of focus can be determined before implementation.

Although exemplary embodiments of the invention have been shown and described, many other changes, modifications and substitutions, in addition to those set forth in the above paragraphs, may be made by one having ordinary skill in the art without necessarily departing from the spirit and scope of this invention.

What is claimed is:

1. An ophthalmic lens for providing a monofocal vision correction power with an enhanced depth of focus, the ophthalmic lens being adapted to be implanted in an eye or to be disposed on or in a cornea and having a central optical axis and a baseline diopter power for far vision correction, the ophthalmic lens comprising:

a first zone surrounding and extending from the central optical axis and having a first vision correction power, the vision correction power at the central optical axis being the baseline optical power;

a second zone located radially outwardly of the first zone and having a second vision correction power which differs from the first vision correction power, one of the first and second vision correction powers being a near vision correction power relative to the baseline diopter power and the other of the first and second vision correction powers being a far, far vision correction power relative to the baseline diopter power;

a third zone located radially outwardly of the second zone and having a third vision correction power which is substantially the same as the first vision correction power; and a fourth zone located radially outwardly of the third zone and having a fourth correction power which is substantially the same as the second vision correction power, the first, second, third and fourth zones being adapted to assist the ophthalmic lens in providing a monofocal vision correction power with an enhanced depth of focus.

2. The ophthalmic lens as recited in claim 1, the first zone comprising a near vision correction power and the second zone comprising an annular far, far vision correction power.

3. The ophthalmic lens as recited in claim 2, a maximum diopter value of the first zone being approximately 0.7 diopters above the baseline diopter power, and a minimum diopter value of the second zone being approximately 0.5 diopters below the baseline diopter power.

4. An ophthalmic lens for providing a monofocal vision correction power with an enhanced depth of focus, the ophthalmic lens having a central optical axis and a baseline diopter power for far vision correction and comprising:

a first zone including, surrounding and extending from the central optical axis and adapted for focusing light only at and in front of a retina of a user; and a second zone located radially outwardly of the first zone and adapted for focusing light in back of the retina of the user, the first and second zones being adapted to assist the ophthalmic lens in providing a monofocal vision correction power with an enhanced depth of focus.

5. The ophthalmic lens as recited in claim 4, further comprising:

a third zone located radially outwardly of the second zone and adapted for focusing light in front of the retina of the user; and a fourth zone located radially outwardly of the third zone and adapted for focusing light in back of the retina of the user, the vision correction power at the central optical axis being the baseline optical power.

6. The ophthalmic lens as recited in claim 5, further comprising:

a fifth zone located radially outwardly of the fourth zone and adapted for focusing light in front of the retina of the user; and a sixth zone located radially outwardly of the fifth zone and adapted for focusing light in back of the retina of the user.

7. An ophthalmic lens for providing a monofocal vision correction power with an enhanced depth of focus, the ophthalmic lens having a central optical axis and a baseline diopter power for far vision correction and comprising:

a first zone surrounding and extending from the central optical axis and adapted for focusing light only in front of a retina of a user; and a second zone located radially outwardly of the first zone and adapted for focusing light in back of the retina of the user, the first and second zones being adapted to assist the ophthalmic lens in providing a monofocal vision correction power with an enhanced depth of focus.

8. The ophthalmic lens as recited in claim 7, further comprising:
   a third zone located radially outwardly of the second zone and adapted for focusing light in front of the retina of the user; and
   a fourth zone located radially outwardly of the third zone and adapted for focusing light in back of the retina of the user.

9. The ophthalmic lens as recited in claim 8, further comprising:
   a fifth zone located radially outwardly of the fourth zone and adapted for focusing light in front of the retina of the user; and
   a sixth zone located radially outwardly of the fifth zone and adapted for focusing light in back of the retina of the user.

* * * * *

UNITED STATES PATENT AND TRADEMARK OFFICE
CERTIFICATE OF CORRECTION

PATENT NO : 6,126,286
DATED : December 19, 2000
INVENTOR(S) : Norito Hasama, et al.

It is certified that error appears in the above-identified patent and that said Letters Patent are hereby corrected as shown below:

On title page, item 75 Inventors
replace "both of Hanno, Japan"
with --both of Saitama, Japan--.

Col. 10, line 62
replace "n FIG. 1"
with --In FIG. 1--.

Col. 28, line 42
replace "11"
with -- 4 --.

Signed and Sealed this

First Day of May, 2001

Attest:

NICHOLAS P. GODICI

Attesting Officer        Acting Director of the United States Patent and Trademark Office

UNITED STATES PATENT AND TRADEMARK OFFICE
CERTIFICATE OF CORRECTION

PATENT NO. : 6,126,286  
DATED : October 3, 2000  
INVENTOR(S) : Valdemar Portney Page 1 of 1

It is certified that error appears in the above-identified patent and that said Letters Patent is hereby corrected as shown below:

This certificate supercedes certificate of correction issued May 1, 2001, the number was erroneously mentioned and should be deleted since no certificate of correction was granted.

Signed and Sealed this

Eighth Day of January, 2002

Attest:

Attesting Officer

JAMES E. ROGAN  
*Director of the United States Patent and Trademark Office*